United States Patent
Molinari et al.

(10) Patent No.: US 9,408,624 B2
(45) Date of Patent: Aug. 9, 2016

(54) INTERVERTEBRAL DISC TREATMENT APPARATUS

(75) Inventors: Michael Molinari, Oxford (GB); Sarit Sivan, Oxford (GB); Dare-Sean Gibbons, Oxford (GB); Manish Arora, Oxford (GB); Jill Urban, Oxford (GB); Constantin Coussios, Oxford (GB)

(73) Assignee: Isis Innovation Limited, Oxford (GB)

( * ) Notice: Subject to any disclaimer, the term of this patent is extended or adjusted under 35 U.S.C. 154(b) by 114 days.

(21) Appl. No.: 14/008,596

(22) PCT Filed: Mar. 30, 2012

(86) PCT No.: PCT/GB2012/050714
§ 371 (c)(1),
(2), (4) Date: Dec. 10, 2013

(87) PCT Pub. No.: WO2012/131383
PCT Pub. Date: Oct. 4, 2012

(65) Prior Publication Data
US 2014/0200505 A1 Jul. 17, 2014

(51) Int. Cl.
*A61B 17/32* (2006.01)
*A61N 7/00* (2006.01)
(Continued)

(52) U.S. Cl.
CPC ... *A61B 17/320068* (2013.01); *A61B 17/22004* (2013.01); *A61N 7/02* (2013.01); *A61B 17/3472* (2013.01); *A61B 2017/00261* (2013.01); *A61B 2017/22008* (2013.01);
(Continued)

(58) Field of Classification Search
CPC ................. A61B 17/22004; A61B 17/320068; A61B 17/3472; A61B 17/22012; A61B 2017/22005; A61B 2017/00261; A61B 2017/22008; A61B 2017/564; A61B 2017/320072; A61B 2017/320076; A61B 2017/22014; A61B 2018/00339; A61B 2019/5276; A61B 2217/005; A61B 2007/0078; A61N 7/02
USPC ............................................ 600/439; 601/2–3
See application file for complete search history.

(56) References Cited

U.S. PATENT DOCUMENTS 5,976,105 A 11/1999 Marcove et al.
6,254,553 B1 7/2001 Lidgren et al.
(Continued)

FOREIGN PATENT DOCUMENTS

GB WO 2012066334 A1 * 5/2012 ........... A61K 9/0009
WO 98/03111 A2 1/1998

OTHER PUBLICATIONS

Hernot, Sophie and Klibanov, Alexander, L. Microbubbles in Ultrasound-Triggered Drug and Gene Delivery. NIH Public Access. Jun. 30, 2008.*

(Continued)

*Primary Examiner* — Melanie Tyson
*Assistant Examiner* — Katherine Schwiker
(74) *Attorney, Agent, or Firm* — Fraser Clemens Martin & Miller LLC; William J. Clemens

(57) ABSTRACT

A method of at least partially removing the nucleus pulposus of an intervertebral disc comprising the nucleus and an annulus surrounding the nucleus is described. The method comprises the steps of: insonating the nucleus with ultrasound thereby to cause at least partial fragmentation of the nucleus; and extracting at least part of the fragmented nucleus. A system for performing the method is also described.

11 Claims, 11 Drawing Sheets

(51) Int. Cl.
  *A61N 7/02* (2006.01)
  *A61B 17/22* (2006.01)
  *A61B 17/34* (2006.01)
  *A61B 17/00* (2006.01)
  *A61B 17/56* (2006.01)
  *A61B 18/00* (2006.01)

(52) U.S. Cl.
  CPC  *A61B 2017/564* (2013.01); *A61B 2018/00339* (2013.01); *A61B 2217/005* (2013.01); *A61N 2007/0078* (2013.01)

(56) References Cited

U.S. PATENT DOCUMENTS

| | | | |
|---|---|---|---|
| 7,211,055 | B2 | 5/2007 | Diederich |
| 7,819,826 | B2 | 10/2010 | Diederich et al. |
| 2006/0095046 | A1 | 5/2006 | Trieu et al. |
| 2008/0027554 | A1* | 1/2008 | Talmadge ............... 623/17.16 |
| 2008/0058942 | A1 | 3/2008 | Yuksel et al. |
| 2009/0177085 | A1* | 7/2009 | Maxwell ........ A61B 17/22004 600/439 |
| 2010/0168571 | A1* | 7/2010 | Savery ............. A61B 8/0841 600/439 |
| 2010/0185087 | A1* | 7/2010 | Nields et al. .............. 600/439 |
| 2010/0324581 | A1 | 12/2010 | Mackool et al. |

OTHER PUBLICATIONS

Hoskins, Peter, Martin, Kevin and Thrush, Abigal. Diagnostic Ultrasound: Physics and Equiptment. New York. Cambridge University Press. 2010. Print.*

* cited by examiner

Fig. 7
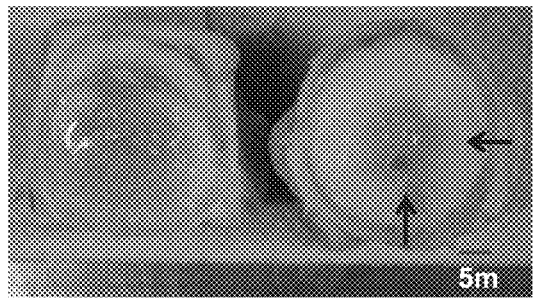

INTERVERTEBRAL DISC TREATMENT APPARATUS

FIELD OF THE INVENTION

The present invention relates to treatment of the intervertebral disc (IVD), and in particular to replacement of the nucleus pulposus (NP) of the IVD.

BACKGROUND TO THE INVENTION

Back pain affects a large proportion of the population, with 4 out of 5 adults reporting back pain at some point in their life, and approximately 7% suffering from chronic non-specific effects. The direct and indirect economic effect of this pain is substantial, with estimates that it could be up to 1-2% of GDP annually. Much chronic, non-specific back pain is believed to derive from a degenerate IVD, which typically includes early degeneration of the NP of the IVD, well before pathological changes in the surrounding annulus fibrosus (AF) are evident.

The two most widely used treatments for IVD-derived back pain are spinal fusion and conservative management. In spinal fusion the pain-generating IVD is largely excised, and the surrounding vertebrae are fused together by various means, for example using a metallic cage screwed onto each. A number of studies show long-term deleterious effects of fusion on adjacent vertebrae and discs; however it is still widely viewed as the 'gold standard' surgical treatment. Conservative management can take many forms, and usually involves a program of stretching, physiotherapy and pain medication. Several high-quality studies have shown minimal difference in outcome between the two treatment protocols, and relatively low levels of improvement for many patients.

There has therefore long been a need for improved management of degenerate disc disease. An obvious conceptual alternative is the surgical removal of the damaged disc, and its replacement with an artificial implant, and some whole-disc implants have FDA approval and are in clinical use. However implantation requires very invasive surgical interventions. Treatments replacing only the NP are minimally invasive and are potentially a useful alternative in many cases. However, studies have shown that these NP implants are prone to fail along the original surgical access track under normal physiological loading of the spine. It is therefore likely that successful replacement of degenerate NP will only be possible if the outer structure of the disc (known as the annulus fibrosus) is conserved during NP insertion.

There is some published literature that discusses the use of high intensity focused ultrasound (HIFU) in treatment of the intervertebral disc. However these papers relate to methods of thermally necrosing nerves in the disc to reduce pain, rather than removal of the IVD NP.

SUMMARY OF THE INVENTION

The present invention provides a method of removing the NP of an intervertebral disc comprising the NP and an annulus fibrosus surrounding the NP, the method comprising the steps of: insonating the NP with ultrasound thereby to cause at least partial fragmentation of the NP; and extracting at least part of the fragmented NP.

The method may comprise injecting cavitation nuclei into the NP prior to the step of insonating the NP. The cavitation nuclei may comprise shells or solid particles of polymeric material. The shells of polymeric material may have particles attached to them so as to provide a rough surface. Alternatively other forms of cavitation nuclei or contrast agents may be used. The cavitation nuclei may be injected using the same needle as is used to extract the fragmented NP, or using a different needle.

The method may further comprise monitoring the NP during the insonation step thereby to monitor the progress of the fragmentation. For example, the monitoring may be performed using at least one of: a single element passive cavitation detector; a multi-element passive cavitation detector; and an imaging system comprising a detector array. Other methods of monitoring may also be used.

The present invention further provides a method of replacing the NP of an intervertebral disc comprising the NP and an annulus fibrosus surrounding the NP, the method comprising the steps of: insonating the NP with ultrasound thereby to cause at least partial fragmentation of the NP; extracting at least part of the fragmented NP; and injecting polymer material to replace the extracted part.

The injecting step may be performed using a needle through which the fragmented tissue of the NP is extracted. This may be the same needle as is used to inject the cavitation nuclei, or it may be a different needle.

The present invention further provides system for removing the NP of an intervertebral disc comprising the NP and an annulus surrounding the NP, the system comprising: at least one source of ultrasound arranged to direct ultrasound into the NP thereby to cause at least partial fragmentation of the NP; and at least one needle arranged to extract a part of the fragmented nucleus.

The present invention further provides a system for replacing the NP of an intervertebral disc comprising the NP and an annulus surrounding the NP, the system comprising: at least one source of ultrasound arranged to direct ultrasound into the NP thereby to cause at least partial fragmentation of the NP; at least one needle arranged to extract a part of the fragmented NP and to inject polymer material into the disc to replace the extracted part.

HIFU-induced fragmentation or ablation, followed by removal and injection of a replacement material, has several advantages over other current and proposed treatments for the degenerate IVD. The surgical access track to the disc is confined to the dimensions of a small-gauge needle, and structural integrity of the annulus is preserved. This increases the chances of restoring normal biomechanical function to the IVD and spine.

Some embodiments of the invention can therefore be used as part of a procedure to replace degenerate material from inside the NP of the patient's IVD. The ultrasound device can be used to non-invasively fragment or ablate the NP material, allowing it to be extracted, for example through a small-gauge needle. In an additional procedure the same needle can in some cases then be used for the injection of a replacement material.

Some embodiments of the invention can incorporate a design of single-element or multi-element transducer that is capable of generating elevated pressures at or near the centre of the IVD, within the NP, without damage to surrounding vertebral bodies or the spinal cord. At low duty cycles, this elevated pressure may be exploited for mechanical fragmentation of collagenous disc material (via acoustic cavitation), whereas at high duty cycles this pressure profile results in enhanced heat deposition which can be exploited either for ablation or for thermal therapy of pain.

Some embodiments involve incorporation of a conventional ultrasound imaging array within the therapeutic probe, which can be used both in active mode and in passive mode. Active mode provides anatomical information for treatment guidance, whilst passive acoustic mapping can provide evidence of successful energy delivery at the right location within the NP and real-time treatment monitoring.

Some embodiments can include injection, in some cases using the same needle to be used for removal of IVD material and injection of a liquid artificial implant, of pressure resistant cavitation nuclei (as described in our UK patent application GB1019434.8, and international patent application No. PCT/GB2011/052244) to promote cavitation effects and thus mechanical fragmentation within the NP. The pressure-resistant feature of the cavitation-promoting agents is important in the context of the present invention as they must be injected against a considerable pressure gradient, which would tend to rupture or damage other types of cavitation nuclei such as shelled micro-bubbles.

The method or system of the invention may further comprise any one or more features, in any combination, of the preferred embodiments, which will now be described by way of example only with reference to the accompanying drawings.

BRIEF DESCRIPTION OF THE DRAWINGS

FIG. 7 is a further set of images of a treated IVD showing a hole formed in the NP;

DESCRIPTION OF THE PREFERRED EMBODIMENTS

Figure 1:
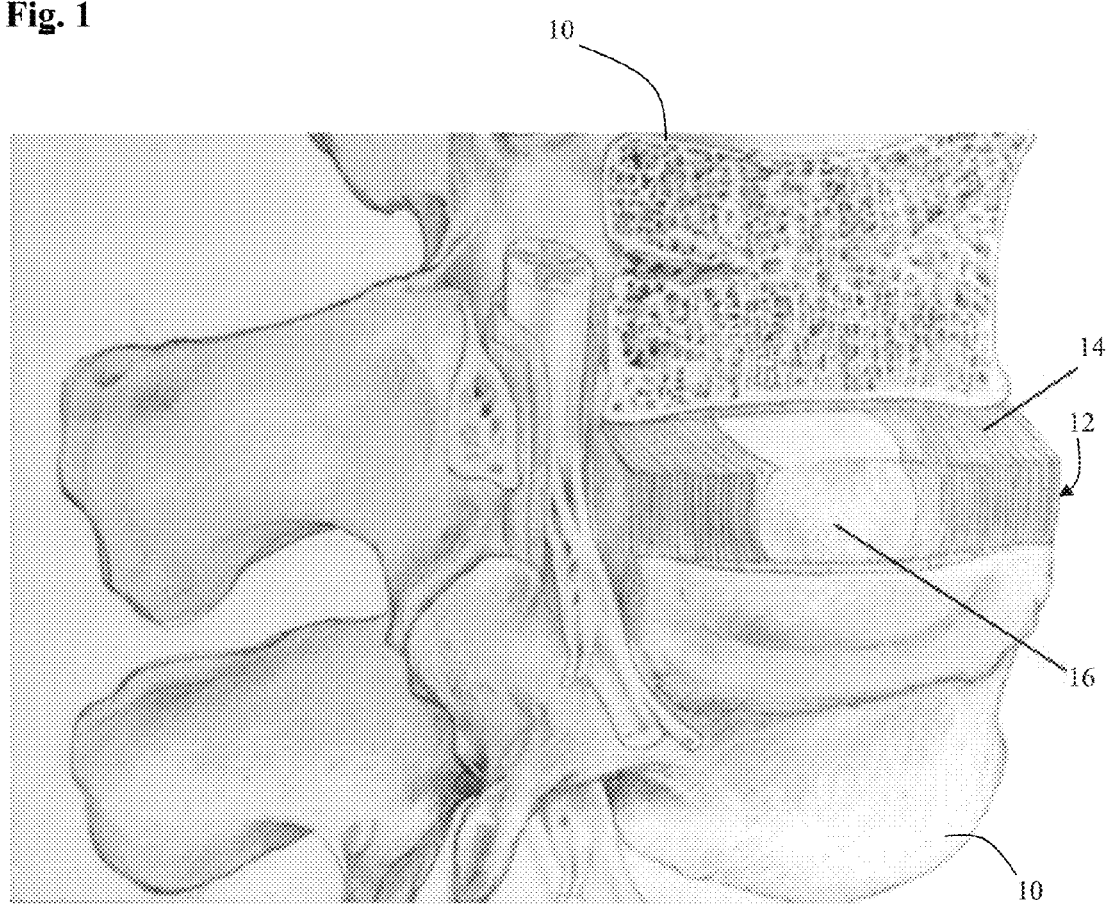
FIG. 1 is a partially cut-away diagram of a section of a human spine showing the structure of the IVD.

Referring to FIG. 1, the spine is made up of a number of vertebrae 10 and between each adjacent pair of vertebrae is an IVD 12 which provides cushioning and support to the vertebrae as the spine flexes. The IVD comprises the annulus fibrosus 14 around its periphery with the NP 16 in the centre. The annulus fibrosus is of a more fibrous tissue and provides support for, and containment of, the NP 16. The IVD further comprises cartilaginous endplates, not shown in the drawings, on the top and bottom surfaces of the IVD, which further contain the NP and provide the upper and lower surfaces of the IVD which contact the vertebrae. In one embodiment of the invention a system and method is provided for insonating the NP 16 so as to fragment the NP, without significantly affecting the surrounding annulus fibrosus 14, so that the NP material can be removed with minimal damage to the annulus fibrosus 14.

Figure 2:
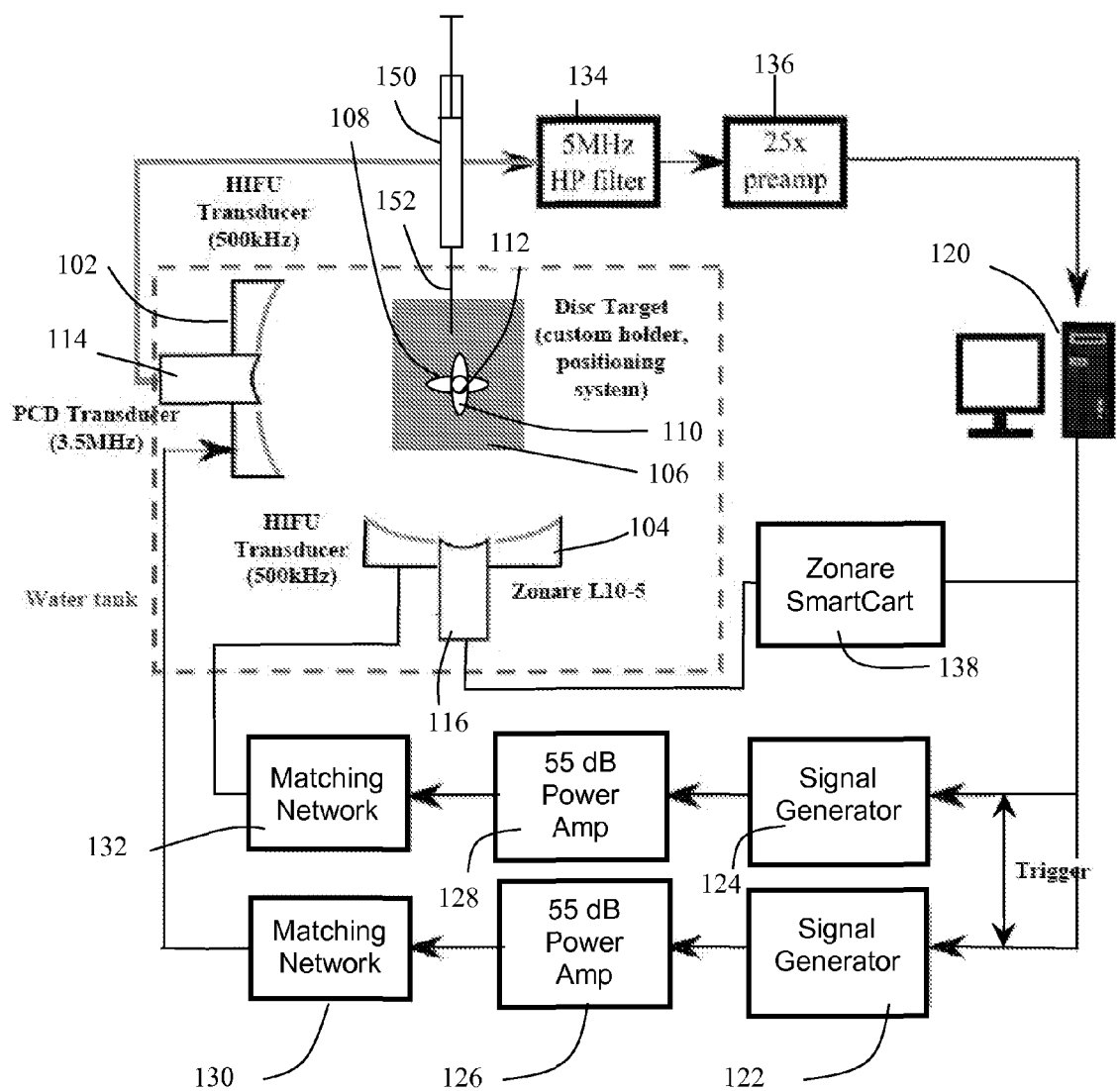
FIG. 2 is a diagram of a system according to an embodiment of the invention for removing and replacing the IVD NP.

Referring to FIG. 2, a system according to one embodiment of the invention comprises first and second therapeutic HIFU ultrasound transducers 102, 104 both arranged to transmit ultrasound towards a target region 106. Each of the transducers 102, 104 has a respective focal region 108, 110 which is approximately circular in cross section but elongated along the axis of the transducer. The transducers 102, 104 are arranged so that the centres of the two focal regions coincide at a focal spot 112. At the centre of one of the transducers 102 is a passive cavitation detector (PCD) 114, arranged coaxially with the transducer, which is arranged to detect ultrasound radiation generated by cavitation induced in an object in the target region 106. At the centre of the other of the transducers 104 is an ultrasound imaging device 114, in this case a Zonare L10-5 detector array which is arranged coaxially with the transducer 104, which is arranged to provide B-mode ultrasound images of the disc and surrounding physiological structures and to map cavitation during HIFU exposure within the object within the target region 106.

A controller 120 in the form of a computer is arranged to control operation of the HIFU transducers 102, 104 and to receive the output signals from the PCD 114 and imaging device 116. Each of the HIFU transducers has associated with it a signal generator 122, 124, a power amplifier 126, 128 and a matching circuit 130, 132. The controller 120 is arranged to transmit trigger signals simultaneously to the two signal generators 122, 124 which are each arranged to generate a control signal the form of which determines the shape of an ultrasound pulse produced by the respective transducer. The control signal is input to the power amplifier 126, 128 which amplifies the signal and inputs it to the respective transducer 102, 104 via the matching circuit 130, 132. The controller 120 is arranged to receive the output of the PCD 114 via a filter 134 and a preamplifier 136 and to receive the output from the imaging device 116 via a processing unit 138.

The apparatus further comprises a syringe 150 having a needle 152 which can be used to inject material into an object in the target region 106, as a target for the therapeutic ultrasound with the transducers 102, 104 being arranged to target the therapeutic ultrasound onto the tip of the needle, and also to extract material from the target region 106. Specifically the syringe is arranged to inject cavitation nuclei into the object in the target region, specifically the NP of the IVD, to extract the material of the IVD when it has been insonated to make it more readily extractable, and to inject material to form a replacement NP.

The procedure of replacement of the damaged NP will now be described. First the syringe 150 is filled with material containing cavitation nuclei. Preferably these are in the form of nanoparticles fabricated from polymer material, such as polydiallyl dimethyl ammonium chloride (PDADMAC), having particles of, for example, silicon dioxide attached to their surfaces to roughen the surface. Details of suitable cavitation nuclei are provided in our UK patent application GB1019434.8 'Sonosensitive nanoparticles' filed on 17 Nov. 2010 (the entire contents of which are incorporated herein by reference). However other types of sonosensitive particles or gas-filled ultrasound contrast agents or other contrast agents can be used. The needle 152 of the syringe is inserted into the NP 16, and the cavitation nuclei are injected into the NP 16 through the needle 152 of the syringe 150. This injection step can be carried out under surgical guidance (typically done under fluoroscopic or endoscopic imaging, but not necessarily). The injection step may also be done using minimally invasive techniques, but not necessarily. The injection is controlled as far as possible so that the cavitation nuclei are confined to the NP and do not spread to the annulus of the IVD.

The needle 152 may then be removed, or it may be left in place during insonation for subsequent use in extracting the fragmented NP tissue.

The therapeutic transducers 102, 104 are then positioned so that their pressure foci 108, 110 coincide at a point 112 inside the NP 16 of the disc to be treated. This may be done using the ultrasound imaging array 116 contained within the therapeutic transducer device 104, but can be achieved using other means of guiding and alignment such as fluoroscopic imaging and/or computer-based patient registration techniques that might not necessarily form part of the therapeutic device, but that can be associated with it.

The transducers 102, 104 are then activated in a controlled manner to mechanically fragment the tissue of the NP 16. This treatment regime is distinct from thermal ablation—it typically uses higher pressure amplitudes delivered in short pulses, with a much lower duty cycle than thermal treatment. The goal of this treatment is explicitly to minimise any thermal effects on the surrounding tissue. The insonation is pulsed with short pulses of three to fifty cycles, low duty ratio of 0.1 to 5% and high pressures of up to 20 MPa peak rarefactional focal pressure (PRFP) or 80 MPa peak positive focal pressure (PPFP). The PRFR may in some cases be anywhere within the range 5-80 MPa, but will generally be less than 50 MPa.

During the insonation, as the NP tissue is being fragmented, the NP is monitored to monitor the location, progress and extent of treatment, and in particular of the fragmentation, using the acoustic sensors contained within the device. In this embodiment these include the single element passive cavitation detector 114 and the multiple element passive cavitation detector 116. However, they can include a B-mode imaging transducer, and an array-based passive detector, for example as described in WO2010/052494.

Once a sufficient amount of the tissue of the NP has been fragmented, the fragmented tissue is extracted. This extraction of the mechanically fragmented tissue can be performed using either the needle 152 that was used initially for the insertion of artificial nuclei, or another needle inserted specifically for the purpose.

In some cases only one insonation and one extraction step may be sufficient. However in other cases, after a first extraction step, further insonation and extraction steps may be performed. In some cases, where repeat insonation steps are performed, further cavitation nuclei are injected for each insonation, though in some cases this may not be necessary.

B-mode or other imaging techniques can be used to check that fragmentation and extraction is complete. Once a sufficient amount of the damaged NP has been extracted, a suitable biocompatible polymer is inserted into the space that has been created within the NP 16. This polymer can be one of a number of suitable polymers, for example protein hydrogels or curable polyurethanes, the defining characteristic of these being that they can be injected in liquid form and undergo in situ hybridization once in place to form a hydrogel that mimics the properties of the healthy NP.

Figure 3:
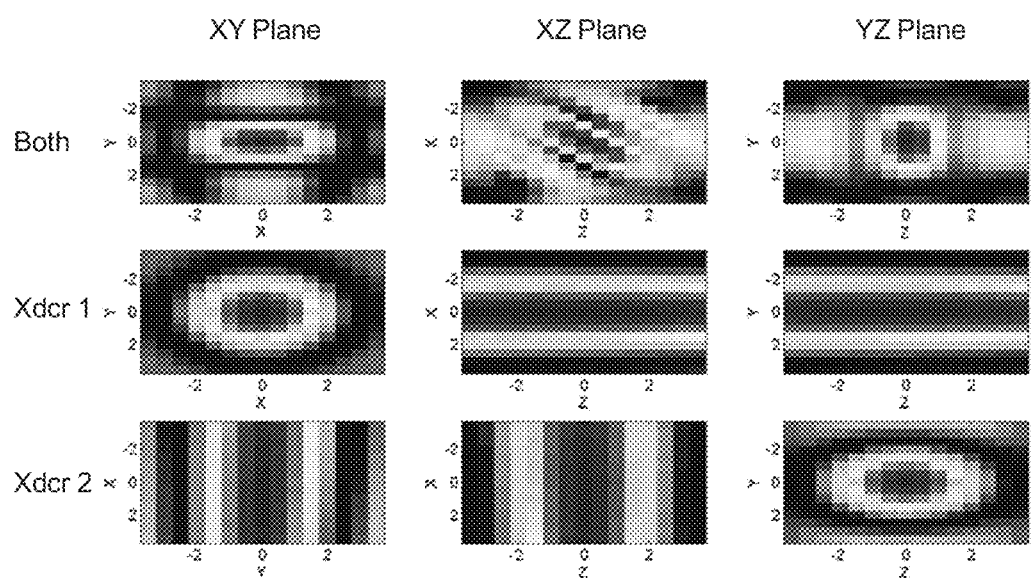
FIG. 3 is a series of plots showing the variation in peak pressure caused by the system of FIG. 2.

Referring to FIG. 3, tests carried out using the system of FIG. 2 show that the acoustic field produced by the dual-transducer configuration is well focused in three dimensions. The two transducers were set up so that they were at right angles to each other, with the first transducer directed in the Z direction (perpendicular to the XY plane) and the second transducer directed in the X direction (perpendicular to the YZ plane). The first row of images are sections through the acoustic field with both transducers transmitting, the second row is with only the first transducer transmitting, and the third row is with only the second transducer transmitting. It can be seen that each transmitter on its own produces an elongated region of acoustic energy, and the two transmitters together produce a focussed spot of acoustic energy. It will be appreciated that the exact shape of the focal spot, and of peaks and troughs within it, can be varied by varying the phases of the two transducers.

Figure 4:
FIG. 4 is an image of cavitation being induced in an IVD using the system of FIG. 2.

FIG. 4 is an image showing cavitation within the IVD NP. This image was produced using a passive cavitation detector as described in WO2010/052494. The outline of the IVD can be seen, as produced using B-mode ultrasound imaging, and the localised cavitation occurs within the square at the centre of the image. This cavitation is produced using transducers located at the top of the image and the right hand side of the image.

Figure 5A:
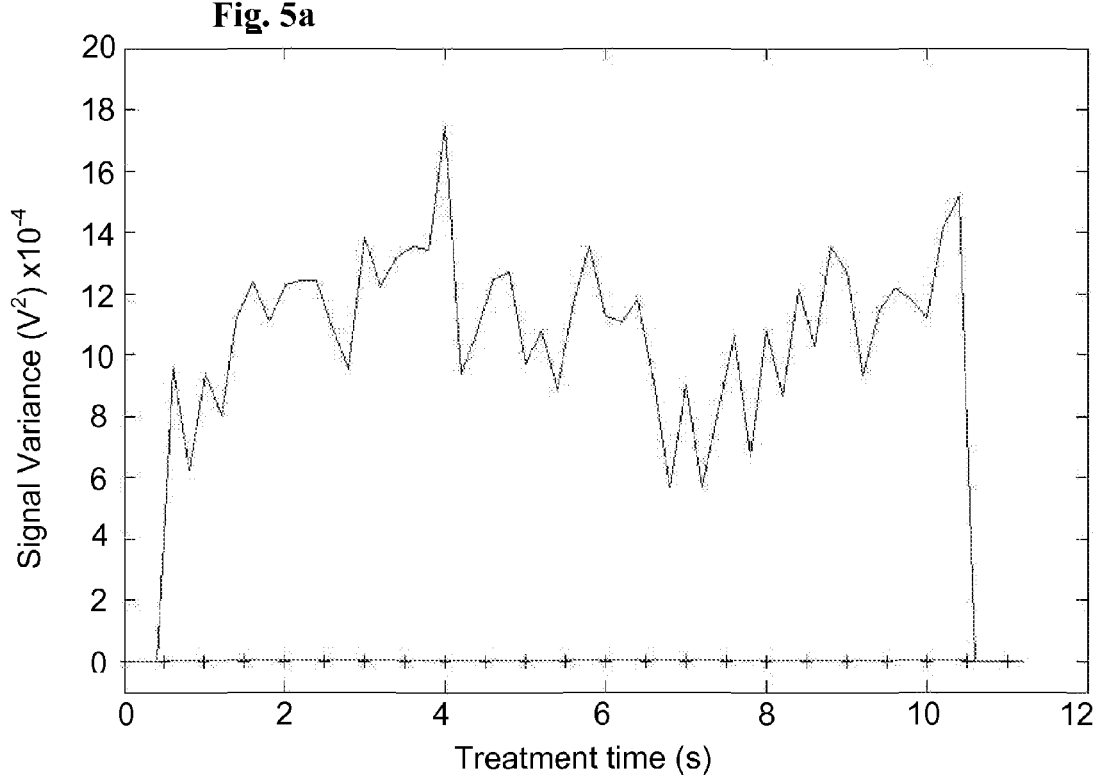
FIGS. 5a, 5b and 5c are plots showing the signals from a passive cavitation detector in the system of FIG. 2.
Figure 5B:
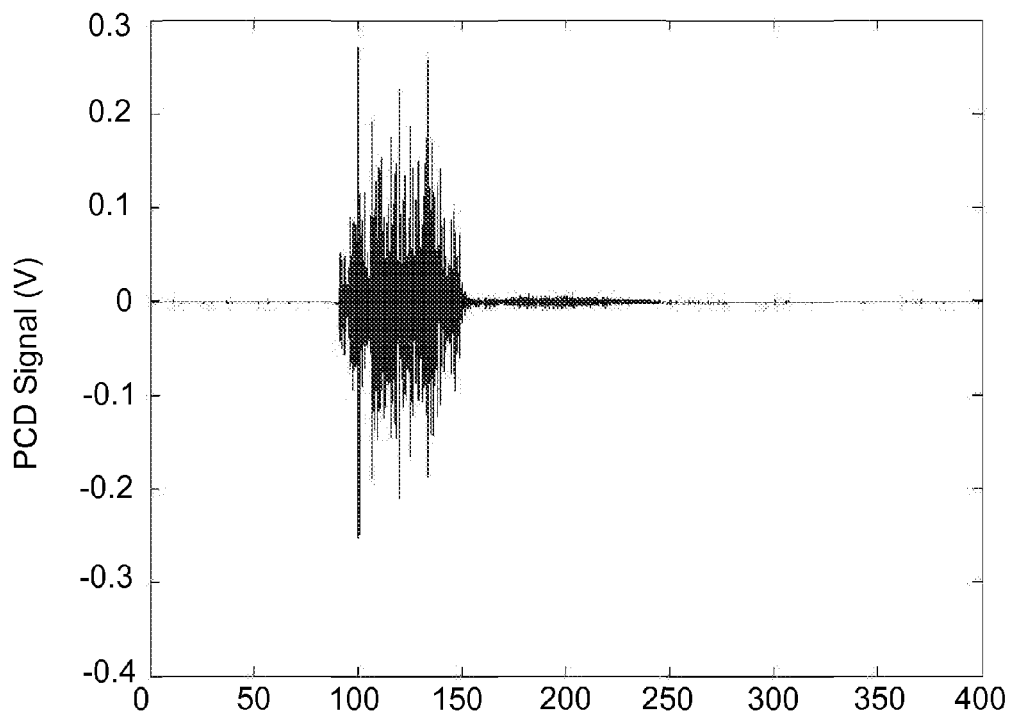
Figure 5C:
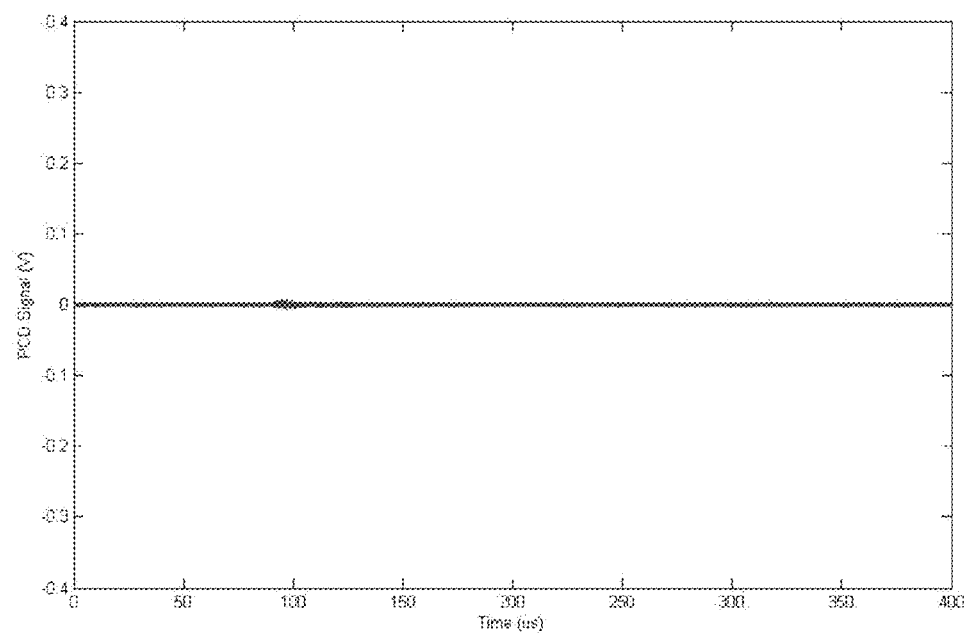

FIGS. 5a, 5b and 5c show the acoustic signals resulting from treatment using the system of FIG. 2 operating at 6.3 MPa PRFP with a 5% duty cycle. FIG. 5a shows the variance of the signal from the PCD 114 over a 10 s treatment time in the presence of artificial cavitation nuclei (upper line), and where water has been injected in the NP (lower line). It also shows the level of background noise in the system with the therapeutic transducers turned off (+markers). The signal variance is a good indicator of cavitation and it can be seen that there is a much higher variance in the presence of nuclei, while in the absence of nuclei the variance is barely above background noise. FIG. 5b shows the PCD signal voltage over the time of a single ultrasound pulse at 4.8 s into the same treatment of the IVD injected with artificial nuclei. The delayed onset of noise from the cavitation activity is due to the time of flight between the transducer and the centre of the disc. FIG. 5c shows the PCD signal voltage over the time of a single ultrasound pulse at 4.8s into the same treatment of the IVD injected with water.

Figure 6:
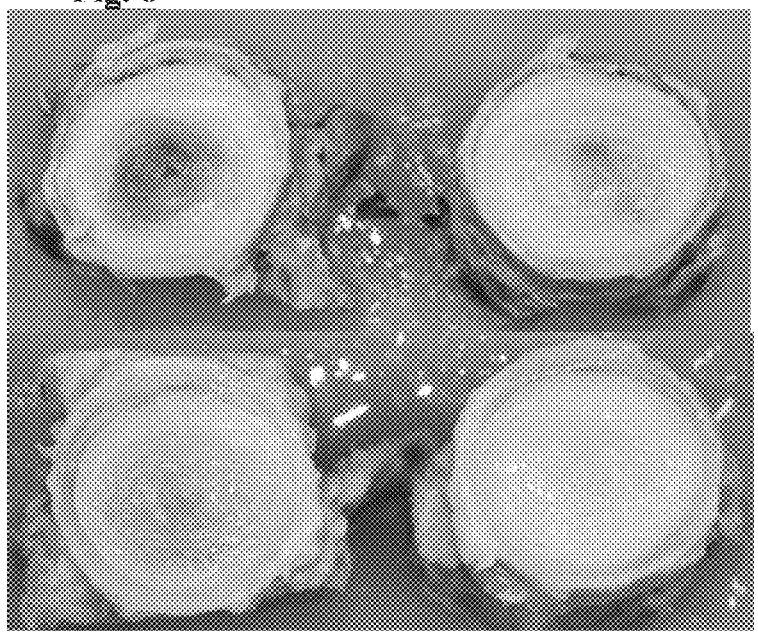
FIG. 6 is a set of images of treated and untreated IVDs.

FIG. 6 shows images of an IVD after removal of NP tissue using the system of FIG. 2 and the treatment shown in FIGS. 5a and 5b. The upper images are of a disc after treatment and the lower images are of a control disc. The cavity in the centre of the treated disc can clearly be seen, as can the lack of damage to the outer areas of the disc.

FIG. 7 shows images of a further IVD after formation of a hole in the NP tissue using the system of FIG. 2.

Figure 8:
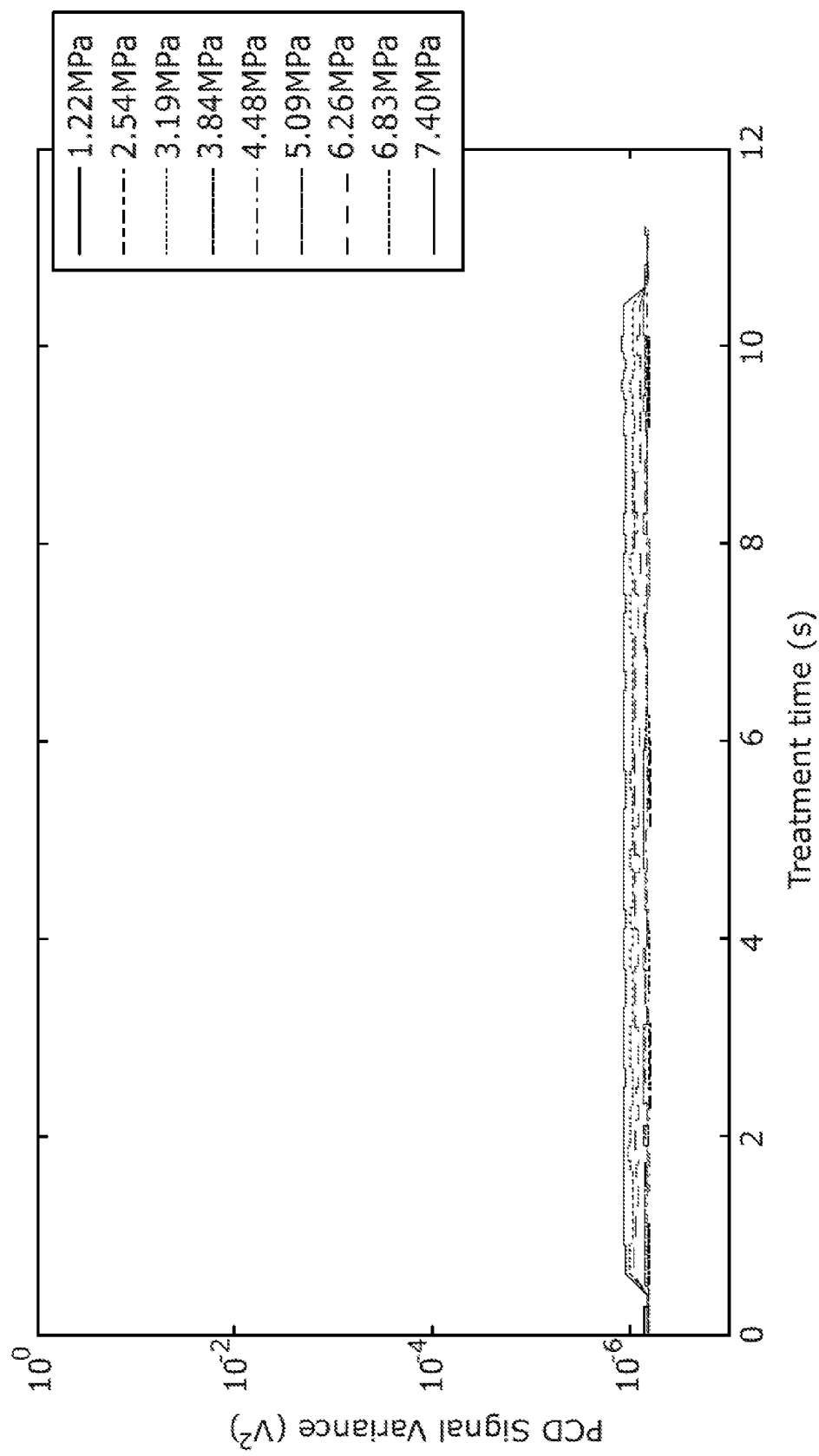
FIG. 8 is a graph showing the level of inertial cavitation over a treatment period in an IVD with no injected fluid, for different ultrasound intensities.
Figure 9:
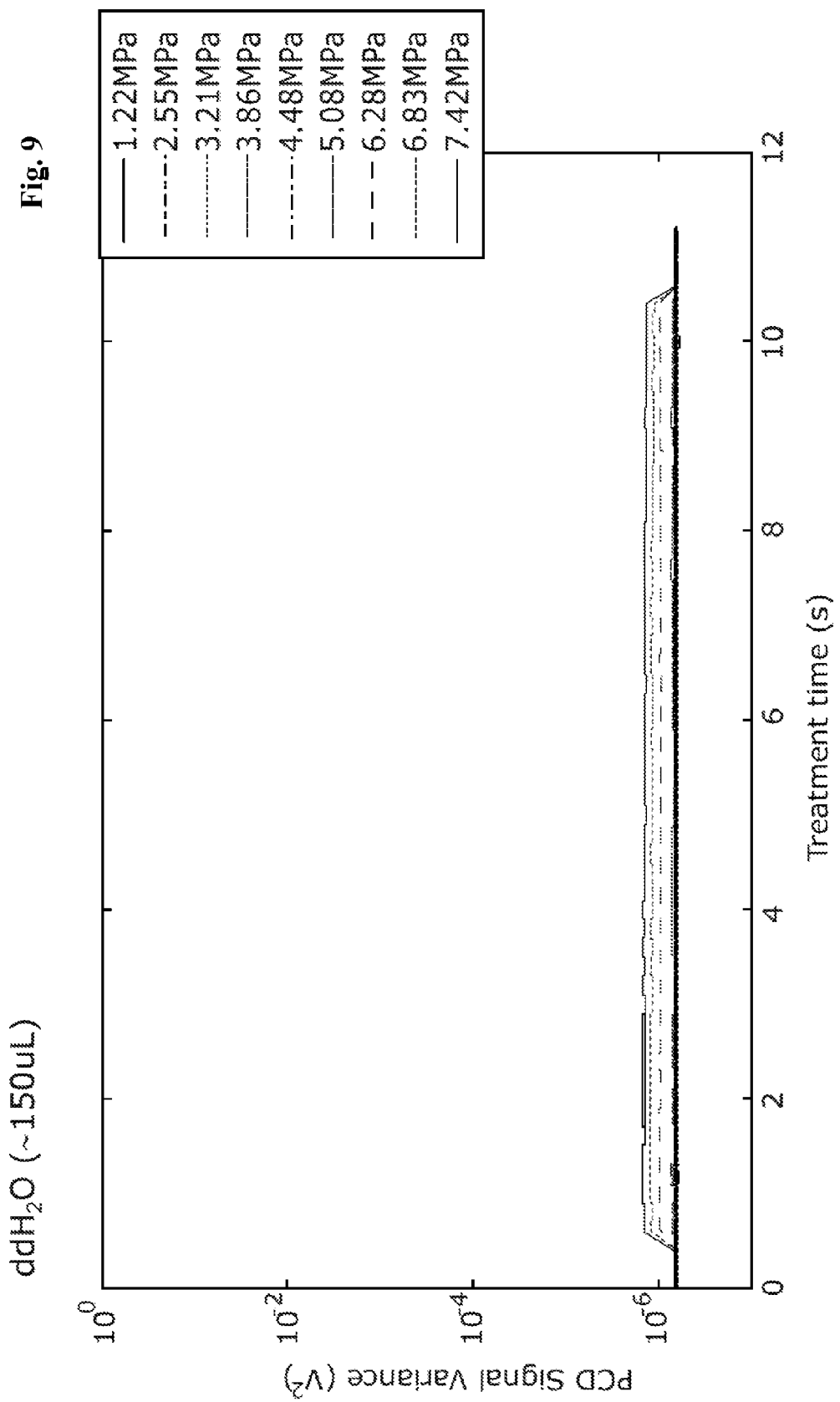
FIG. 9 is a graph similar to FIG. 8 showing results after injection of de-ionized water.
Figure 10:
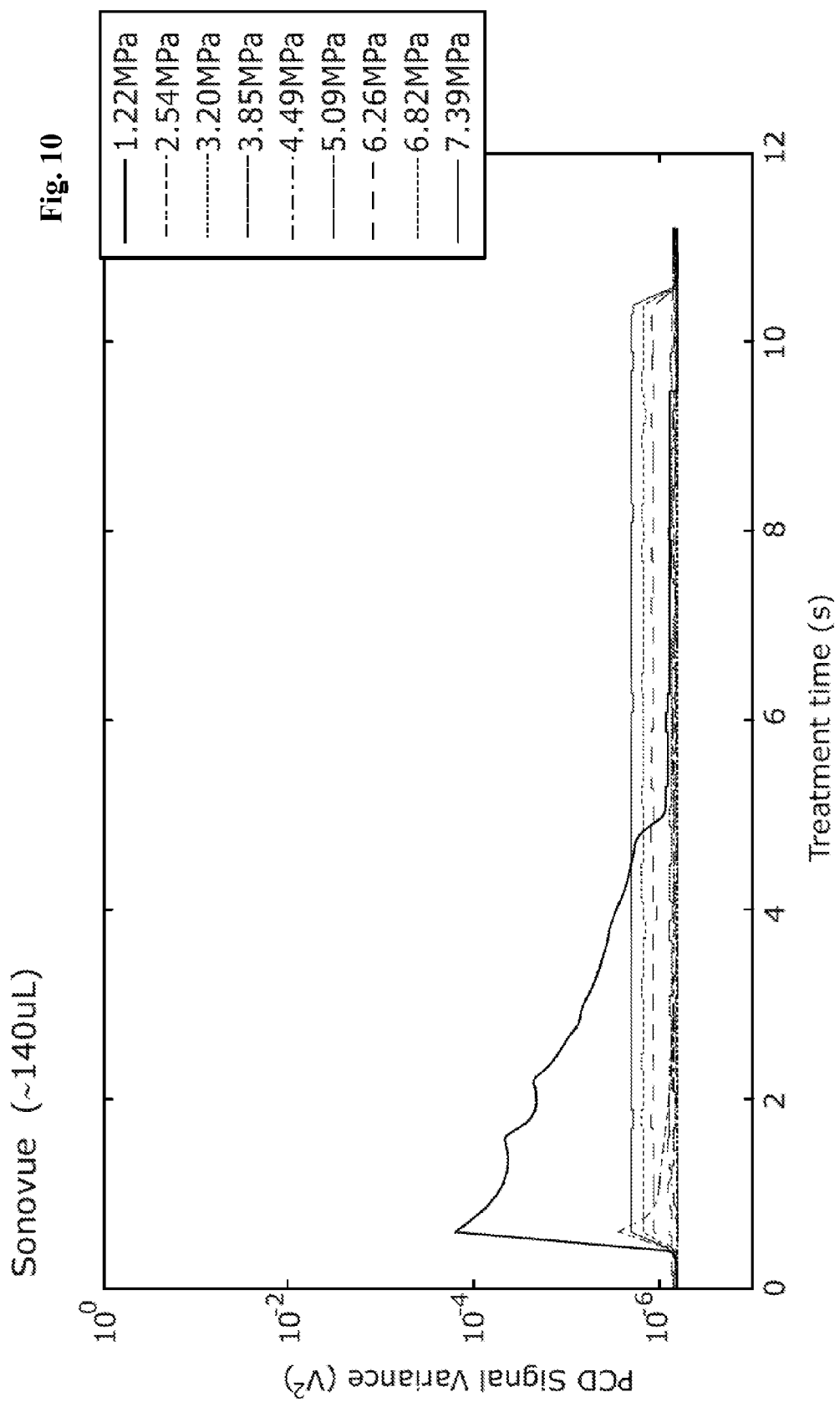
FIG. 10 is a graph similar to FIG. 8 showing results after injection of commercially available Sonovue contrast agent.
Figure 11:
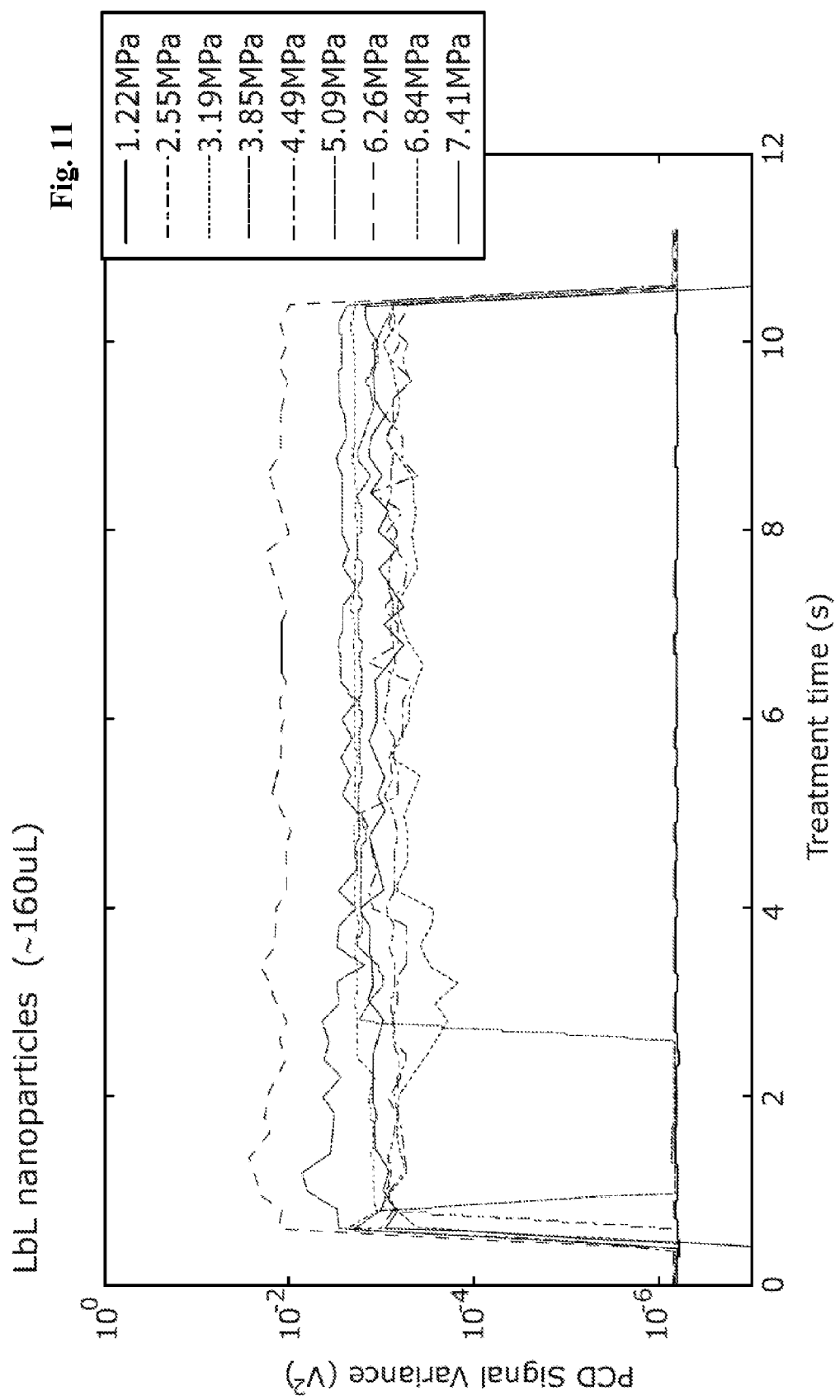
FIG. 11 is a graph similar to FIG. 8 showing results after injection of sonosensitive nanoparticles.

Referring to FIGS. 8 to 11 further experiments were performed using the system of FIG. 2, operating with 5% duty ratio and 25 cycles per pulse, and IVDs which had been injected with different contrast agents. The level of cavitation activity was measured over a ten second insonation period, in each case using ultrasound of a range of different intensities. FIG. 8 shows the results for no contrast agent, FIG. 9 shows the results for water as a contrast agent, FIG. 10 shows the results for Sonovue contrast agent, and FIG. 11 shows the results for sonosensitive nanoparticles. As can be seen, cavitation activity is found to be of considerably greater intensity and remains sustained throughout the ultrasound exposure with the sonosensitive nanoparticles only.

The treatment method described in this embodiment relies on high-amplitude ultrasound fields that induce inertial cavitation in the NP, i.e. the formation and inertial collapse of cavities inside the focal region of the transducers. Under the regime described, the mechanical forces involved in the collapse of the cavities cause the tissue in the local region to be fragmented thus allowing it to be removed through a needle. The device is also capable of exploiting these elevated pressure fields to cause mild hyperthermia or ablation within the disc, in the presence or absence of cavitation.

The system described in this embodiment uses a multiple-treatment-transducer configuration to produce a tightly-focussed acoustic field with sufficient amplitude to induce inertial cavitation inside the target region. It also employs several passive transducer elements in an array configuration to allow for localisation of cavitation activity and mapping of the treated region. As described above, a needle in the focal region can also be used to help target the therapeutic ultrasound, to inject proprietary particles that lower the cavitation threshold and to potentially remove any fragmented disc material.

The invention claimed is:

1. A method of at least partially removing the nucleus pulposus of an intervertebral disc comprising the nucleus and an annulus surrounding the nucleus, the method comprising the steps of:
   injecting pressure resistant cavitation nuclei into the nucleus;
   insonating the nucleus including the pressure resistant cavitation nuclei with ultrasound thereby to cause at least partial fragmentation of the nucleus; and
   extracting at least part of the fragmented nucleus.

2. The method according to claim 1 wherein the cavitation nuclei comprise shells of polymeric material.

3. The method according to claim 2 wherein the shells of polymeric material have particles attached to them so as to provide a rough surface.

4. The method according to claim 1 further comprising monitoring the nucleus during the insonation step thereby to monitor the progress of the fragmentation.

5. The method according to claim 4 wherein the monitoring is performed using a multi-element passive cavitation detector.

6. The method according to claim 1 further comprising injecting polymer material to replace the extracted part.

7. The method according to claim 6 wherein the injecting step is performed using a needle through which the fragmented nucleus is extracted.

8. A system for replacing the nucleus of an intervertebral disc comprising a nucleus and an annulus surrounding the nucleus, the system comprising:
   a source of pressure resistant cavitation nuclei of polymer material for injection into the nucleus;
   at least one source of ultrasound arranged to direct ultrasound into the nucleus thereby to cause cavitation in the nucleus and at least partial fragmentation of the nucleus;
   a passive cavitation detector array arranged to image the nucleus; and
   at least one needle arranged to extract a part of the fragmented nucleus and the at least one needle or another needle arranged to inject said polymer material into the disc to replace the extracted part.

9. The system according to claim 8 wherein the at least one needle is arranged both to extract said part of the fragmented nucleus and to inject said polymer material.

10. A method of at least partially removing the nucleus pulposus of an intervertebral disc comprising the nucleus and an annulus surrounding the nucleus, the method comprising the steps of:
    injecting pressure resistant cavitation nuclei into the nucleus;
    insonating the nucleus with ultrasound thereby to cause cavitation in the nucleus and at least partial fragmentation of the nucleus;
    imaging the nucleus during the insonation step using a passive cavitation detector; and
    extracting at least part of the fragmented nucleus.

11. The method according to claim 10 further comprising imaging the nucleus with active ultrasound imaging.

* * * * *